United States Patent [19]

Kimura

[11] Patent Number: 4,921,424

[45] Date of Patent: May 1, 1990

[54] DENTAL HANDPIECE

[75] Inventor: Hiroshi Kimura, Osaka, Japan

[73] Assignee: G-C Dental Industrial Corp., Tokyo, Japan

[21] Appl. No.: 213,924

[22] Filed: Jun. 30, 1988

[30] Foreign Application Priority Data

Sep. 2, 1987 [JP] Japan .................................. 62-218060

[51] Int. Cl.$^5$ .............................................. A61C 1/05
[52] U.S. Cl. ..................................... 433/114; 433/85; 433/126
[58] Field of Search ..................... 433/114, 81, 84, 85, 433/86, 87, 119, 126, 132

[56] References Cited

U.S. PATENT DOCUMENTS

| | | | |
|---|---|---|---|
| 3,924,335 | 12/1975 | Balamuth et al. ................... | 433/119 |
| 4,017,974 | 4/1977 | Sotman et al. ........................ | 433/85 |
| 4,075,761 | 2/1978 | Behne et al. ......................... | 433/126 |
| 4,148,143 | 4/1979 | Fleer .................................... | 433/132 |
| 4,182,038 | 1/1980 | Fleer .................................... | 433/126 |
| 4,490,113 | 12/1984 | Kawada .............................. | 433/126 |

Primary Examiner—John J. Wilson
Attorney, Agent, or Firm—Oblon, Spivak, McClelland, Maier & Neustadt

[57] ABSTRACT

A detachable head having therein an air turbine and connecting pipes extending sideways therefrom and a synthetic resin grip provided at its end with a connecting portion having connecting holes into which the connecting pipes of the head are inserted, the dental handpiece having a structure in that a fluid-passage tube formed of a flexible synthetic resin and having a fibrous reinforcing material embedded in its wall is to be connected at its one end with a dental unit body, and passes at least through the synthetic resin grip and is caused to communicate at its other end with the connecting holes in the connecting portion.

11 Claims, 2 Drawing Sheets

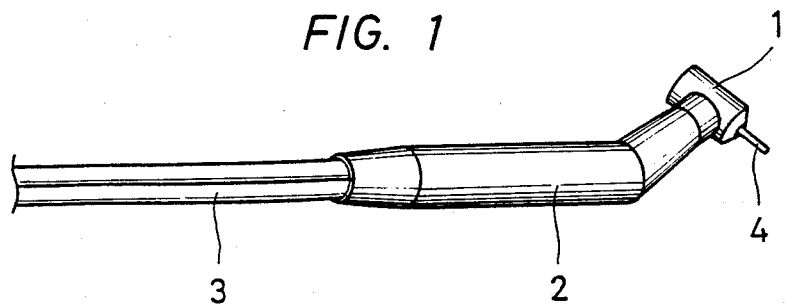
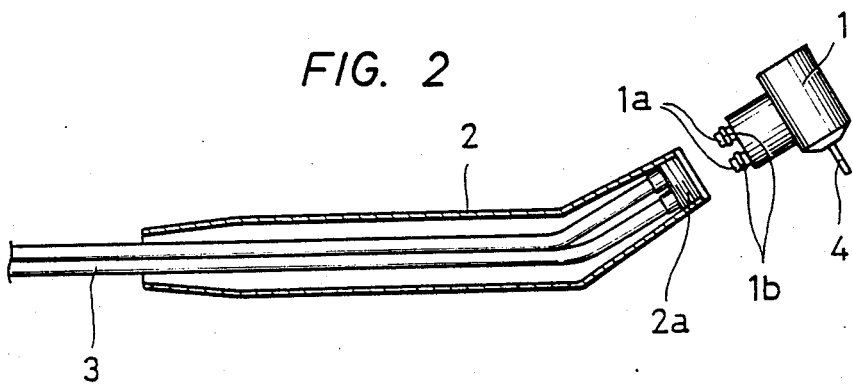# 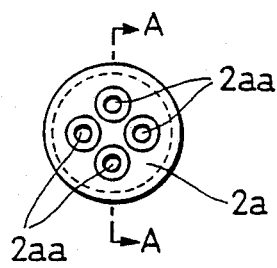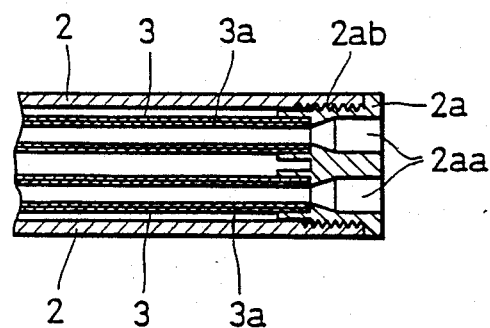

DENTAL HANDPIECE

BACKGROUND OF THE INVENTION

1. Field of the Invention

The present invention relates to a compressed air drive type dental handpiece which is light in weight and easy to handle.

2. Statement of the Prior Art

Generally, the dental handpiece designed to be driven by compressed air is broken down into two- and four-hole types which include respectively two and four fluid paths extending from a tube for fluid passage connected with the body of a dental unit to the head of a dental handpiece body. The fluids flowing through these paths in the case of the two-hole type are compressed air pressurized to 2 to 5 kg/cm$^2$ and supplied for driving an air turbine that is a rotary member built in the head and cooling water pressurized to 1.5 to 2.5 kg/cm$^2$ and sprayed from a nozzle of the head. In addition to the paths for the fluids used in the aforesaid two-hole type, the four-hole type includes those for chip air and exhausting the compressed air used for driving the air turbine built in the head.

The fluid-passage tube for flowing such fluids therethrough should possess conflicting properties, say, sufficient pressure resistance and flexibility that permits the dental handpiece to yield easily within such a degree that its manipulation properties are not impaired, while preventing its premature deterioration or breaking. Urethane rubber, silicone rubber, vinyl chloride rubber, etc. have been used as the materials to this end with, usually, the thickness thereof of 1 mm or more. The fluid-passage tube is of the structure wherein a detachable, metallic connector is fixed to the end of a connecting pipe extending from the rear end of a grip of the dental handpiece.

Such a conventional dental handpiece is considerably heavy, partly because the fluid-passage tube, metallic connector and handpiece body are weighty in themselves, and partly because the length of the fluid-passage tube connected at its one end with a dental unit body and at its other end with the rear end of the grip thereof through the metallic connector is regulated to about 1.5 m, taking into account the manipulation properties of the handpiece at the time when used by the user such as a dentist, and the fluid paths in the fluid-passage tubes are filled therein with compressed air, cooling water and so on when the handpiece is used. This has been primarily responsible for the problems that while handpiece is used, it is pulled rearward so that the user bears a heavy burden and thus becomes fatigued, and it degrades in manipulation properties.

SUMMARY OF THE INVENTION

The present inventors have made extensive studies to solve the aforesaid problems, and found out that the problems with the conventional dental handpiece are that:

the fluid-passage tube connected at its one end with a dental unit body is increased in wall thickness and heavy, the handpiece is complicated in structure and heavy, and should be of high accuracy, since the metallic connector fixed to the end of the tubes has to be detachably attached to the rear end of the grip of the handpiece with good air- and fluid-tightness, and the handpiece body is weighty because of being formed of brass or stainless steel.

In order to solve these problems, the present inventors have successfully developed a dental handpiece which is light in weight, well-balanced and convenient to use by:

forming a fluid-passage tube to be connected at its one with a dental unit body of a flexible synthetic resin material having a fibrous reinforcing material embedded in its wall, whereby it is reduced in wall thickness and weight, and constructing a dental handpiece body of a detachable head including therein an air turbine and connecting pipes sideways therefrom and a synthetic resin grip provided at its end with a connecting portion having connecting holes into which the connecting pipes of the head are fitted, and passing the synthetic resin tube for fluid passage at least through the synthetic resin grip and causing it to communicate at its other end with the connecting holes in the connecting portion, whereby a conventional heavy, metallic connector can be replaced with the light connecting portion provided with the holes into which the connecting pipes of the detachable head are fitted, and a conventional heavy, metallic dental handpiece grip can be replaced with the light synthetic resin grip, while the light synthetic resins tube for fluid passage, which is caused to communicate with the connecting holes in the connecting portion, is passed at least through the synthetic resin grip, and is made integral with or fixed to the connecting portion.

More specifically, the present invention relates to a dental handpiece including a detachable head having therein an air turbine and connecting pipes sideways therefrom and a synthetic resin grip provided at its end with a connecting portion having connecting holes into which said connecting pipes of said head are inserted, said dental handpiece being characterized in that a fluid-passage tube formed of a flexible synthetic resin and having a fibrous reinforcing material embedded in its wall is to be connected at its one end with a dental unit body, and passes at least through said synthetic resin grip and is caused to communicate at its other end with said connecting holes in said connecting portion.

BRIEF DESCRIPTION OF THE DRAWINGS

The aforesaid and other objects and features of the present invention will be understood from a reading of the following description with reference to the accompanying drawings, which are given for the purpose of illustration alone, and in which:

FIG. 1 is a perspective view of one embodiment of the dental handpiece according to the present invention, FIG. 2 is a side view showing in section only the synthetic resin grip of the dental handpiece according to the present invention, from which its head is removed, FIG. 3 is an enlarged front view showing the shape of the end portion of one embodiment of the synthetic resin grip, FIG. 4 is a sectional view taken along the line A—A of FIG. 3.

DETAILED DESCRIPTION OF PREFERRED EMBODIMENTS

Some embodiments of the dental handpiece according to the present invention will now be explained in more detail with reference to the accompanying drawings.

Figure 7:
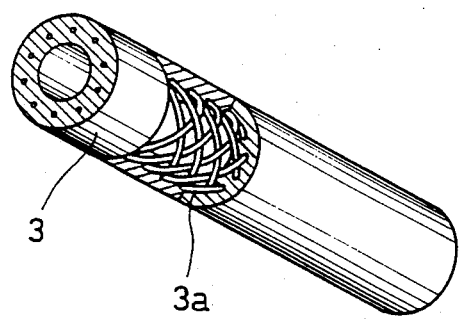
FIG. 7 is a perspective view showing the structure of the synthetic resin tube for fluid passage which is used with the dental handpiece according to the present invention.

Referring to the drawings, reference numeral 1 stands for a detachable head having side connecting pipes 1a provided therearound with O-rings 1b and including therein an air turbine (not shown) driven by compressed air, and 2 a grip of synthetic resin having at its one end a connecting portion 2a having therein connecting holes 2aa into which the connecting pipes 1a with the O-rings 1b are fitted. As illustrated in FIG. 7, a flexible synthetic resin tube 3, through which a fluid is to flow, is to be connected at its one end with a dental unit body (not shown), and has a wall thickness of usually 0.2 mm to 0.5 mm, which is formed of an engineering resin such as a polysulfone, polyphenylene sulfide or polyether sulfone resin and a fibrous reinforcing material 3a of 10 $\mu$m to 20 $\mu$m in thickness embedded therein, such as roving cloth or filament windings made of, e.g., glass, aramide or carbon fibers. The synthetic resin tube 3 is passed at least through the grip 2 and is allowed to communicate at its other end with the connecting holes 2aa in the connecting portion 2a provided at the end of the grip 2. A cutting tool 4 is rotatably driven by the air turbine, while it extends from the detachable head 1. The cutting tool 4 may be either of the type that is designed to be attached to or detached from a chuck of the detachable head 1, if any, or the type that is fixed to the air turbine included in the detachable head 1. In the latter case, once the cutting tool 4 wears out, it is replaced with a new one for each detachable head 1 or the air turbine fixedly provided with a cutting tool.

For the communication of the other end of the synthetic resin tube 3 for fluid passage passed at least through the synthetic resin grip 2 with the connecting holes 2aa in the connecting portion 2a thereof, the connecting portion 2a may either be formed by a connector member fixed to the other end of the tube 3 as the connecting holes 2aa, as illustrated in FIGS. 3 and 4, or be made integral with the other end of the tube 3 as the connecting holes 2aa. According to one example of forming such a connector member, molding tools (not shown), each for a connector member provided with a columnar projection having a conical apex, are used in combination while taking into consideration of number, thickness and position of the connecting pipes 1a extending sideways from the detachable head 1. They are then positioned in place with the projections being inserted in the open end of the synthetic resin tube 3 for fluid passage. Finally, a synthetic resin is cast and cured in the spaces of the molding tools to mold the connector members simultaneously with the fixation thereof to the tube 3. Referring to the synthetic resin materials used, both tube 3 and connector members should preferably be formed of engineering resins such as polysulfone, polyphenylene sulfide and polyether sulfone resins, for example. It is noted, however, that general-purpose resins, e.g., vinyl chloride, melamine, phenolic and ABS resins, may be used for the connector members. In an alternative embodiment, the synthetic resin tube 3 for fluid passage may be firmly fitted and fixed onto premolded connector members with adhesives. In this embodiment, it is preferable that the synthetic resin grip 2 is threadedly connected with the outer peripheries of the connector members by means of screws 2ab. However, it goes without saying that such connection may be achieved by the use of adhesives without provision of any threaded portion. Such a structure eliminates the need of using an engineering resin of high dimensional accuracy as the material for the synthetic resin grip 2, and makes it possible to freely employ general-purpose plastics which are cheaper than engineering resins.

Figure 5:
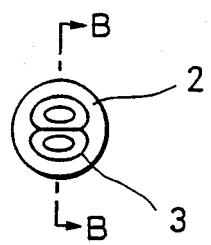
FIG. 5 is an enlarged front view showing the shape of the end portion of another embodiment of the synthetic resin grip.
Figure 6:
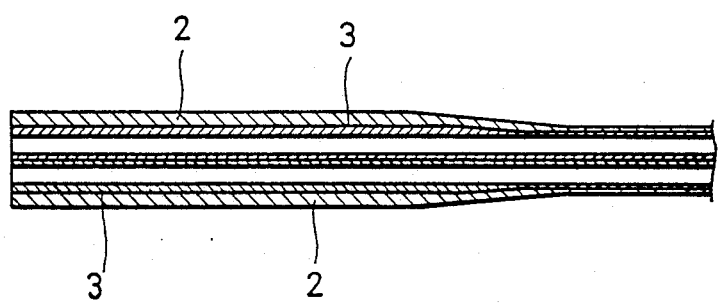
FIG. 6 is a sectional view taken along the line B—B of FIG. 5.

Turning now to the embodiment shown in FIGS. 5 and 6, the synthetic resin tube 3 for fluid passage is prepared by simultaneous extrusion molding. At this time, the shape of a resin melt in a pouring basin is conformed to that of the synthetic resin grip 2, whereby the position and size of fluid passage holes are conformed to those of the connecting holes 2aa accommodative to the connecting pipes 1a extending sideways from the detachable head 1. The thus formed synthetic resin tube 3 for fluid passage and the synthetic resin grip 2 adjacent thereto are integral with each other, and include the connecting portion 2a and holes 2aa at their joining ends. In this embodiment, the synthetic resin material used should preferably be an engineering resin as earlier mentioned.

EFFECT AND ACTION OF THE INVENTION

The dental handpiece of such a structure according to the present invention can be used in the quite same manner as a conventional dental handpiece formed of a metal and provided at its rear end with a metallic connector and a thick wall tube for fluid passage. According to the present invention, nonetheless, the dental handpiece, which has until now been heavy because of being formed of brass or stainless steel and complicated in structure and costly due to the need of providing a separate fluid path therein, can be considerably simplified in structure and reduced in weight owing to the materials used, since it comprises in combination the detachable head 1 which is similar in structure to that of the body of a conventional dental handpiece, except that the connecting pipes 1a extend sideways therefrom; the synthetic resin grip 2 having at its end the connecting portion 2a provided with the connecting holes 2aa into which the connecting pipes 1a of said head 1 are fitted; and the portion passing through said grip 2 corresponding to an extension of the synthetic resin tube 3 for fluid passage which is connected at its one end with a dental unit and caused to communicate at its other end with said connecting holes 2aa in said connecting portion 2. Further, the conventional heavy connector formed of a metal can be replaced with the light connecting portion 2a provided with the connecting holes 2aa into which the connecting pipes 1a of the detachable head 1 are fitted, and the heavy tube for fluid passage due to a large wall thickness can be replaced with the flexible synthetic resin tube 3 for fluid passage which is reduced in thickness and weight by embedding the fibrous reinforcing material 3a in the wall thereof, whereby the total weight of the handpiece can be considerably reduced in weight. Still further, the present dental handpiece is held in a well-balanced state, since its center of gravity is shifted towards its head. For that reason, it is unlikely that the handpiece may be pulled rearward in use so that the user bears a heavy burden or thus becomes fatigued, or its manipulation properties degrade.

The dental handpiece of such a structure according to the present invention can be supplied at low costs, since only the head 1 with a built-in air turbine, which is the most important working part for the intended purpose, is made detachable, thereby enabling the mass-production of the parts other than the detachable head 1. If required, a chucked detachable head 1 with a built-in air turbine may be used to freely replace the cutting tool 4. Further, a number of the detachable heads 1 each including a built-in air turbine and a fixed cutting tool 4 may be provided so as to prevent run-out or cooscillation of the cutting tool 4, which occur due to the fact that whenever it is attached to the chuck, the depth to which the cutting tool 4 is inserted differs from one cutting tool to another. This permits the cutting tool 4 to be replaced with a new one in an easy and assured manner. Still further, the identification of the detachable head 1 and synthetic resin grip 2 may be improved by coloring them in correspondence to the shape and type of the cutting tool 4.

The dental handpiece according to the present invention has various advantages, as mentioned above, and makes a great contribution to dentistry.

What is claimed is:

1. A dental handpiece including a detachable head having an air turbine therein and connecting pipes extending sideways therefrom and a synthetic resin grip having at its end a connecting portion provided therein with connecting holes into which said connecting pipes of the head are fitted, wherein:
   a tube for fluid passage formed of a flexible synthetic resin and having a fibrous reinforcing material embedded in its wall is to be connected at its one end to a dental unit body, and passes at least through said grip and is caused to communicate at its other end with said connecting hole in said connecting portion.

2. A dental handpiece as recited in claim 1, wherein said connecting portion is made integral with the end of said synthetic resin tube for fluid passage as said connecting hole.

3. A dental handpiece as recited in claim 1, wherein said connecting portion is a connector member fixed to the end of said synthetic resin tube for fluid passage.

4. A dental handpiece as recited in any one of claims 1 to 3, wherein said fibrous reinforcing material embedded in the wall of said synthetic resin tube for fluid passage is of a roving cloth of glass fibers.

5. A dental handpiece as recited in any one of claims 1 to 3, wherein said fibrous reinforcing material embedded in the wall of said synthetic resin tube for fluid passage is a filament winding of glass fibers.

6. A dental handpiece as recited in any one of claims 1 to 3, wherein said fibrous reinforcing material embedded in the wall of said synthetic resin tube for fluid passage is of a roving cloth of aramide fibers.

7. A dental handpiece as recited in any one of claims 1 to 3, wherein said fibrous reinforcing material embedded in the wall of said synthetic resin tube for fluid passage is a filament winding of aramide fibers.

8. A dental handpiece as recited in any one of claims 1 to 3, wherein said fibrous reinforcing material embedded in the wall of said synthetic resin tube for fluid passage is of a roving cloth of carbon fibers.

9. A dental handpiece as recited in any one of claims 1 to 3, wherein said fibrous reinforcing material embedded in the wall of said synthetic resin tube for fluid passage is a filament winding of carbon fibers.

10. A dental handpiece as recited in any one of claims 1 to 3, wherein said detachable head is provided with a chuck to or from which a cutting tool is attached or detached.

11. A dental handpiece as recited in any one of claims 1 to 3, wherein a cutting tool is fixed to said air turbine of said detachable head.

* * * * *